United States Patent [19]

Maurer et al.

[11] 4,348,538

[45] Sep. 7, 1982

[54] PREPARATION OF 3-BROMO-4-FLUORO-BENZALDEHYDE ACETALS AND INTERMEDIATES THEREFOR

[75] Inventors: Fritz Maurer, Wuppertal; Uwe Priesnitz, Solingen; Hans-Jochem Riebel; Bernd Gallenkamp, both of Wuppertal; Erich Klauke, Odenthal, all of Fed. Rep. of Germany

[73] Assignee: Bayer Aktiengesellschaft, Leverkusen, Fed. Rep. of Germany

[21] Appl. No.: 302,913

[22] Filed: Sep. 16, 1981

[30] Foreign Application Priority Data

Sep. 24, 1980 [DE] Fed. Rep. of Germany ....... 3035921

[51] Int. Cl.$^3$ ................ C07C 59/153; C07C 43/313; C07C 119/10; C07C 121/76
[52] U.S. Cl. ............... 562/459; 260/544 D; 260/544 F; 260/545 R; 564/272; 568/592
[58] Field of Search ........................ 568/592; 564/272; 562/459; 260/545 R

[56] References Cited

U.S. PATENT DOCUMENTS

| 4,108,877 | 8/1978 | Klink et al. ................ 260/545 R X |
| 4,218,469 | 8/1980 | Fuchs et al. ................ 424/304 |
| 4,234,739 | 11/1980 | Photis et al. ................ 562/459 X |

Primary Examiner—Dolph H. Torrence
Attorney, Agent, or Firm—Sprung, Horn, Kramer & Woods

[57] ABSTRACT

A process for the preparation of a 3-bromo-4-fluoro-benzaldehyde acetal of the formula:

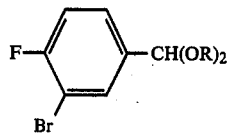

in which
R each independently is a $C_1$ to $C_4$ alkyl group or the radicals R together are a $C_2$ to $C_5$ alkanediyl radical, comprising reacting 3-bromo-4-fluoro-phenylglyoxylic acid of the formula:

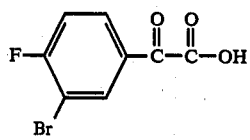

with an amine of the formula:

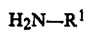

in which
$R^1$ is an alkyl, cycloalkyl or aryl radical, at a temperature between about 0° and 200° C. to produce a 3-bromo-4-fluoro-benzaldimine of the formula:

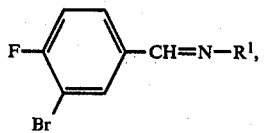

and reacting that with an alcohol or alkanediol of the formula:

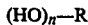

in which n is 1 or 2 in the presence of sulphuric acid at a temperature between about 0° and 100° C. Various of the reactants are new and syntheses are given.

18 Claims, No Drawings

PREPARATION OF 3-BROMO-4-FLUORO-BENZALDEHYDE ACETALS AND INTERMEDIATES THEREFOR

The invention relates to an unobvious process for the preparation of 3-bromo-4-fluoro-benzaldehyde acetals, to 3-bromo-4-fluoro-benzaldimines as well as 3-bromo-4-fluoro-phenylglyoxylic acid and 3-bromo-4-fluoro-benzoyl cyanide as new intermediate products for this process and to processes for their preparation.

It is known that 4-fluoro-3-phenoxy-benzaldehyde, which is an intermediate product for pesticidally active pyrethroids, is obtained when 4-fluoro-3-phenoxy-benzyl bromide is reacted with hexamethylenetetramine and the product of this reaction is heated with acids (see U.S. Pat. No. 4,218,469). However, the yield in this synthesis method is unsatisfactory, as is the case in the preparation of the starting compound from 4-fluoro-3-phenoxytoluene and N-bromo-succinimide.

3-Bromo-4-fluoro-benzaldehyde and acetals thereof as well as 4-fluoro-3-phenoxy-benzaldehyde acetals, as new intermediate products for the preparation of 4-fluoro-3-phenoxy benzaldehyde, are the subject of U.S. application Ser. No. 174,762, filed Aug. 4, 1980, abandoned.

The present invention now provides a process for the preparation of 3-bromo-4-fluoro-benzaldehyde acetals of the general formula:

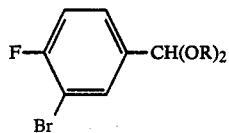

(I)

in which each radical R independently represents a $C_1$ to $C_4$ alkyl group or the radicals R together represent a $C_2$ to $C_5$ alkanediyl radical
which is characterized in that
(a) a 3-bromo-4-fluoro-benzaldimine of the general formula:

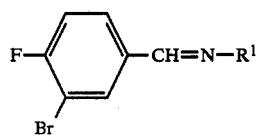

(II)

in which $R^1$ represents an optionally branched and/or optionally cyclic and/or optionally substituted alkyl group, or represents an optionally substituted aryl radical,
is reacted with an alcohol or alkanediol of the general formula:

(HO)$_n$—R  (III)

in which
R has the abovementioned meaning and
n is 1 or 2,
in the presence of sulphuric acid at a temperature between 0° and 100° C., or
(b) 3-bromo-4-fluoro-phenylglyoxylic acid of the general formula:

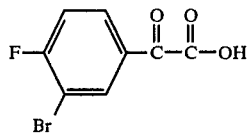

(IV)

is reacted with an amine of the general formula:

H$_2$N—R$^1$  (V)

in which
$R^1$ has the abovementioned meaning, if appropriate in the presence of a diluent, at a temperature between 0° and 200° C., and the crude products thereby obtained, which contain the compound of the formula (II), are reacted with an alcohol of the formula (III) in the presence of sulphuric acid, at a temperature between 0° and 100° C.

The present invention further provides, as new compounds, the 3-bromo-4-fluoro-benzaldimines of the general formula:

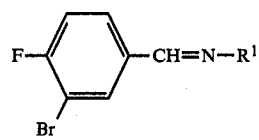

(II)

in which $R^1$ represents an optionally branched or optionally cyclic and optionally substituted alkyl group, or represents an optionally substituted aryl radical.

The present invention further provides a process for the preparation of the compounds of the formula (II) according to the present invention which is characterized in that:
(i) 3-bromo-4-fluoro-benzaldehyde of the formula:

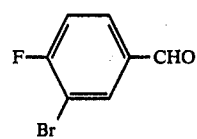

(VI)

is reacted with an amine of the formula (V), as defined above, if appropriate in the presence of a diluent, or (ii) 3-bromo-4-fluoro-phenylglyoxylic acid of the formula (IV) as given above, is reacted with an amine of the formula (V), as defined above, if appropriate in the presence of a diluent at a temperature between 0° and 200° C.

The present invention further provides as a new compound, 3-bromo-4-fluoro-phenylglyoxylic acid of the formula:

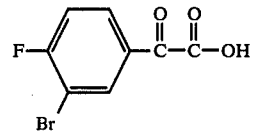

(IV)

The present invention also provides a process for the preparation of 3-bromo-4-fluoro-phenylglyoxylic acid, which is characterized in that 3-bromo-4-fluoro-benzoylcyanide of the formula:

variant (a) or 3-bromo-4-fluoro-phenylglyoxylic acid and aniline and then ethanol for reaction variant (b);

(VII)

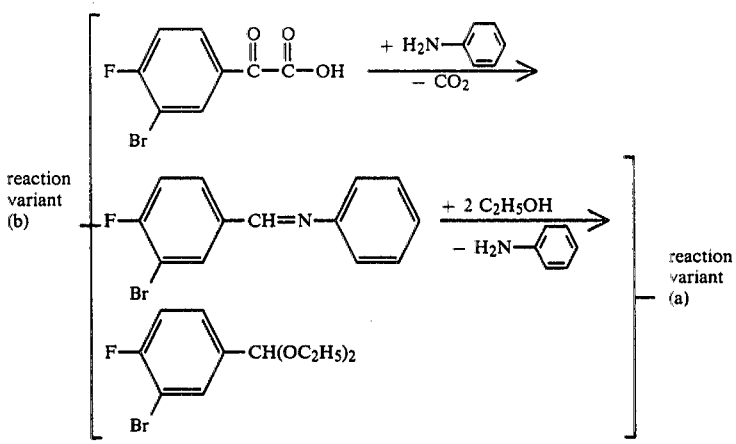

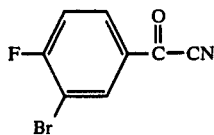

(VII)

is reacted with hydrochloric acid or sulphuric acid.

The present invention further provides, as a new compound, 3-bromo-4-fluoro-benzoyl cyanide of the formula:

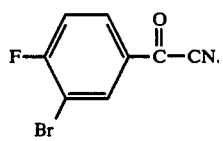

(VII)

The present invention also provides a process for the preparation of 3-bromo-4-fluoro-benzoyl cyanide, which is characterized in that a 3-bromo-4-fluoro-benzoyl halide of the formula:

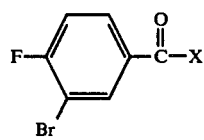

(VIII)

in which X represents a fluorine, chlorine or bromine atom, is reacted with sodium cyanide or potassium cyanide.

Surprisingly, 3-bromo-4-fluoro-benzaldehyde acetals can be prepared in a simpler manner and in higher yields by the process according to the invention, via the new 3-bromo-4-fluoro-benzaldimines, than by the above-mentioned methods. Advantages of the new process are, above all, that inexpensive starting materials or reactants can be used, no reducing agents or oxidizing agents are necessary and it is possible to carry out the acetalization without additional auxiliaries, such as ortho-esters.

The process according to the present invention for the preparation of 3-bromo-4-fluoro-benzaldehyde is illustrated by the following equation, using N-phenyl-3-bromo-4-fluoro-benzaldimine and ethanol for reaction The reaction variant (a) is carried out at a temperature between 0° and 100° C., preferably at a temperature between 10° and 50° C.

Examples which may be mentioned of alcohols and alkanediols of formula (III) used as starting substances in reaction variant (a) are: methanol, ethanol, n- and iso-propanol, n-, iso-, sec.- and tert.-butanol and ethane-1,2-diol, propane-1,3-diol and 2,2-dimethylpropane-1,3-diol.

Methanol, ethanol and ethane-1,2-diol are the preferred starting substances.

The alcohols of the formula (III) are employed in excess in order to dilute the reaction mixtures. In general, up to 80 moles, preferably up to 40 moles, of alcohol of the formula (III) are employed per mole of aldimine of the formula (II).

Generally between 0.5 and 1.5 moles, preferably between 0.5 and 1 mole, of sulphuric acid are also used per mole of aldimine of the formula (II).

In a preferred embodiment of reaction variant (a), the 3-bromo-4-fluoro-benzaldimine of the formula (II) is initially introduced into the reaction vessel in an alcohol of the formula (III), and sulphuric acid is slowly metered into this solution. The reaction mixture is stirred until the reaction has ended.

Working up can be carried out by customary methods. For example, the alcohol is distilled off, under reduced pressure, and the residue is diluted with an organic solvent which is virtually immiscible with water, such as, for example, toluene, and the undissolved material is filtered off. The filtrate is washed (for example with aqueous potassium carbonate solution), dried and filtered and the filtrate is evaporated.

The products of the formula (I) are then obtained by vacuum distillation of the residue.

The first stage of the reaction variant (b) is preferably carried out using a diluent. Possible diluents are virtually any of the inert organic solvents. These include, in particular, aliphatic and aromatic, optionally halogenated hydrocarbons (such as pentene, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene), ethers (such as diethyl ether and dibutyl ether, glycol dimethyl ether and diglycol dimethyl ether, tetrahydrofuran and dioxane), and amides (such as dimethylformamide and dimethylacetamide).

The reaction temperature can be varied within the substantial range of 0° and 200° C. and is preferably a temperature between 50° and 150° C.

In general, 0.9 to 1.5 moles, preferably 0.95 to 1.2 moles of amine of the formula (V) are employed per mole of phenylglyoxylic acid of the formula (IV).

In a preferred embodiment of the first stage of reaction variant (b), 3-bromo-4-fluoro-phenylglyoxylic acid of formula (IV) is initially introduced into the reaction vessel in one of the abovementioned diluents at a temperature between 50° and 100° C., and the amine of the formula (V) is added at this temperature. The reaction mixture is heated until the decarboxylation reaction has ended, and the solvent is then removed carefully by distillation under reduced pressure. The crude product of the formula (II) thereby obtained as the residue is then converted into the product of the formula (I) as described for reaction variant (a).

Preferred 3-bromo-4-fluoro-benzaldimines to be used as starting substances in reaction variant (a) and preferred corresponding amines of formula (V) to be used as starting substances in reaction variant (b), are those in which $R^1$ represents a $C_5$ or $C_6$ cycloalkyl radical, or a phenyl radical which is optionally substituted by methyl, ethyl, chlorine and/or nitro.

Examples of the aldimines of the formula (II) which may be mentioned are: N-cyclopentyl-, N-cyclohexyl-, N-phenyl-, N-(4-methyl-phenyl)-, N-(3-methyl-phenyl)-, N-(2-methyl-phenyl)-, N-(4-chloro-phenyl)-, N-(4-nitro-phenyl)-, N-(3-nitro-phenyl)- and N-(2,6-diethyl-phenyl)-3-bromo-4-fluoro-benzaldimine.

Examples of the amines of the formula (V) which may be mentioned are: cyclopentylamine, cyclohexylamine, aniline and 2-methyl-, 3-methyl-, 4-methyl-, 4-chloro-, 4-nitro-, 3-nitro-, and 2,6-diethyl-aniline.

The process according to the invention for the preparation of the new 3-bromo-4-fluoro-benzaldimines of formula (II) is illustrated by the following equation, using 3-bromo-4-fluoro-benzaldehyde and aniline as starting substances for reaction variant (i) or 3-bromo-4-fluoro-phenylglyoxylic acid aniline as starting substances for reaction variant (ii):

reaction variant (i)

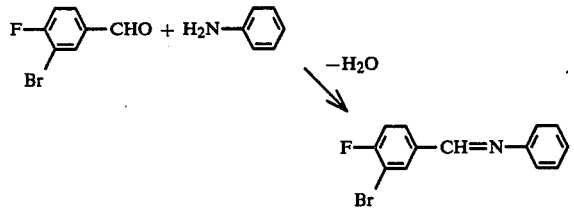

reaction variant (ii)

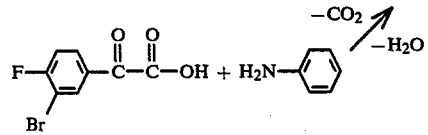

The diluents used on both variants (i) and (ii) are preferably the inert organic solvents mentioned above.

The reaction temperature can be varied within a substantial range in both variants (i) and (ii). In general, the reaction is carried out at a temperature between 0° and 200° C., preferably at a temperature between 50° and 150° C.

In general, between 0.9 and 1.5 moles, preferably 0.95 to 1.2 moles, of amine of the formula (V) are employed per mole of 3-bromo-4-fluoro-benzaldehyde or 3-bromo-4-fluoro-phenylglyoxylic acid.

In a preferred embodiment of reaction variant (i) 3-bromo-4-fluoro-benzaldehyde is heated to the boiling point with an amine of the formula (V) in one of the abovementioned diluents, preferably in a solvent which is suitable for separating off the water azeotropically, such as toluene, until the reaction has ended, the water formed as a by-product preferably being removed via a water separator. The products of the formula (II) are isolated by carefully distilling off the volatile components under reduced pressure.

The procedure of reaction variant (ii) is as described above, for the first stage of reaction variant (b) for the preparation of 3-bromo-4-fluoro-benzaldehyde acetals.

The 3-bromo-4-fluoro-benzaldehyde (VI) to be used as the starting substance is the subject of U.S. application Ser. No. 174,762, filed Aug. 4, 1980, abandoned.

The 3-bromo-4-fluoro-phenylglyoxylic acid which is used as the starting compound in reaction variant (ii) is obtained by reacting 3-bromo-4-fluoro-benzoyl cyanide with hydrochloric acid or sulphuric acid, preferably hydrochloric acid. The temperature is in general kept at a temperature between 0° and 100° C., preferably between 20° and 80° C. 1 to 2 liters of one of the acids mentioned, in a concentration of between 30 and 60 percent by weight, are generally employed per mole of 3-bromo-4-fluoro-benzoyl cyanide. If necessary, the acid concentration is increased during the reaction by passing in hydrogen chloride gas.

In order to carry out the process described above for the preparation of 3-bromo-4-fluoro-phenylglyoxylic acid, the mixture of reactants is generally stirred at 20° to 30° C. for several hours and then heated to 70° to 80° C. for several hours. When the reaction mixture is cooled to 20° C., 3-bromo-4-fluoro-phenylglyoxylic acid precipitates out in the form of crystals and can be isolated by filtration.

The 3-bromo-4-fluoro-benzoyl cyanide required as the starting material in process for the preparation of 3-bromo-4-fluoro-phenylglyoxylic acid is obtained by reacting 3-bromo-4-fluoro-benzoyl halides of the formula (VIII), as defined above, with sodium cyanide or potassium cyanide.

This reaction is generally carried out at a temperature between 0° and 150° C., preferably between 20° and 120° C.

0.9 to 1.5 moles, preferably 1 to 1.2 moles of alkali metal cyanide are employed per mole of halide of the formula (VIII).

In order to carry out the process for the preparation of 3-bromo-4-fluoro-benzoyl cyanide, the reactants are preferably mixed at 20° C. and the mixture is heated to a temperature between 50° and 120° C. until the reaction has ended. After cooling, the mixture is filtered. The product of the formula (VII), which is in the filtrate, is obtained in pure form by vacuum distillation.

3-Bromo-4-fluoro-benzoic acid halides of the formula (VIII), as defined above, which are to be used as starting substances, are the subject of our prior, as yet unpublished, patent application (corresponding to German patent application No. P 29 15 738).

A mixture of 3-bromo-4-fluoro-benzoic acid fluoride and bromide is obtained, for example, when 4-chloro-benzoyl chloride is converted into 4-fluoro-benzoyl fluoride by reaction with potassium fluoride and the 4-fluoro-benzoyl fluoride is then brominated.

4-Chloro-benzoyl chloride is reacted with potassium fluoride, for example, in tetramethylene sulphone at a temperature between 200° and 220° C. and the reaction mixture is worked up by distillation. 4-Fluoro-benzoyl fluoride of boiling point 53° C./20 mbars (refractive index $n_D^{20}=1.4792$) is obtained.

4-Fluoro-benzoyl fluoride is reacted with elementary bromine in the presence of 1% of iron-III chloride at 70° to 75° C. In a batch of 1 mole, 40 g of unchanged starting material and 182 g of a mixture of 3-bromo-4-fluoro-benzoyl fluoride (boiling point: 82°–83° C./15 mbars; refractive index $n_D^{20}=1.5315$; melting point: 32°–34° C.) and 3-bromo-4-fluorobenzoyl bromide (boiling point: 123° C./15 mbars; melting point: 35°–37° C.) remain after distillation.

The 3-bromo-4-fluoro-benzaldehyde acetals of the formula (I), as defined above, can be used for the preparation of 3-phenoxy-4-fluoro-benzaldehyde, which is as an intermediate product for insecticides (see U.S. Pat. No. 4,218,469), it being possible for 3-phenoxy-4-fluoro-benzaldehyde acetals to be isolated as intermediate products.

The preparation of 3-phenoxy-4-fluoro-benzaldehyde can be outlined by the following equation, using, for example, 3-bromo-4-fluoro-benzaldehyde diethyl acetal and potassium phenolate as starting substances in a first stage and with acetal splitting with an acid, such as hydrochloric acid to be carried out as a second stage:

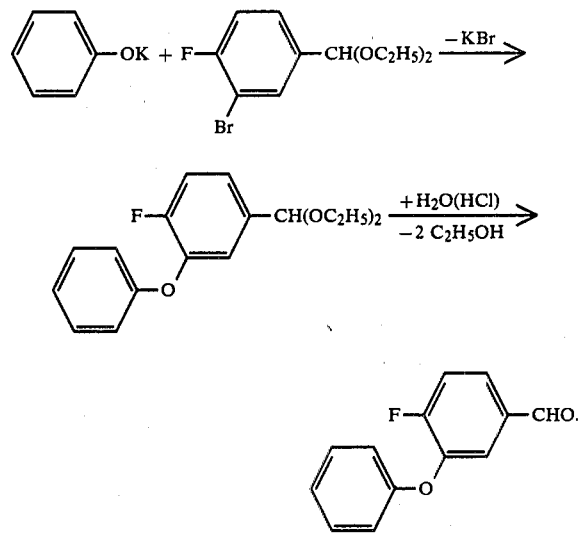

Alkali metal compounds and alkaline earth metal compounds of phenols which can be used as starting substances in this process are, for example, sodium phenolate, potassium phenolate and magnesium phenolate.

Copper or copper compounds are used as catalysts. Examples of these catalysts which may be mentioned are copper, copper-I oxide, copper-II oxide, copper-I chloride and copper-I-bromide.

Aprotic polar solvents are preferably used as the diluents. Examples of these solvents are dimethylformamide, dimethylacetamide, N-methylpyrrolidone, dimethylsulphoxide, tetramethylene sulphone, hexamethylphosphoric acid triamide and bis-(2-methoxyethyl) ether (diglyme). The latter is particularly preferred.

The reaction temperature is kept between 100° and 200° C., preferably between 130° and 170° C. The process is usually carried out under normal pressure.

1 to 2 moles, preferably 1.2 to 1.8 moles, of phenolate, 0.01 to 0.5 mole, preferably 0.1 to 0.5 mole, of copper catalyst and 100 to 500 ml of diluent are employed per mole of 3-bromo-4-fluoro-benzaldehyde acetal of the formula (I).

In a preferred embodiment of the reaction described, the phenolate is initially introduced into the reaction vessel in one of the abovementioned diluents, together with the copper catalyst, and the mixture is heated to the reaction temperature. The 3-bromo-4-fluoro-benzaldehyde acetal is then added dropwise and the reaction mixture is subsequently stirred for some hours. Working up can be effected by customary methods, for example by a procedure in which the diluent is distilled off under reduced pressure, the residue is dissolved in toluene, the solution is filtered and the filtrate is washed with dilute sodium hydroxide solution and distilled under reduced pressure. The 3-phenoxy-4-fluoro-benzaldehyde acetals are thus obtained as colorless liquids.

Saponification of the acetals to 3-phenoxy-4-fluoro-benzaldehyde can be carried out by customary methods. In a preferred procedure, the acetals are mixed with a dilute mineral acid, such as hydrochloric acid or sulphuric acid, and the mixture is stirred at temperatures between 20° and 60° C. for several hours. For working up, the mixture is extracted with an organic solvent which is virtually immiscible with water (such as toluene) and the extracts are washed with sodium bicarbonate solution and water and freed from the solvent by distillation under reduced pressure. 3-Phenoxy-4-fluoro-benzaldehyde remains as an oily residue.

PREPARATIVE EXAMPLES

EXAMPLE 1

4-Fluoro-3-bromo-benzoyl cyanide 177 g (3.6 moles) of sodium cyanide and 663 g (3 moles) of 3-bromo-4-fluorobenzoyl fluoride were together initially introduced into the reaction vessel and were heated. At about 80° C., an exothermic reaction started, which had to be restrained somewhat by slight cooling. The temperature was allowed to rise to 100° C. and the mixture was stirred at 100° C. for 1 hour. The exothermic reaction continued for about 10 minutes, and additional heat had then to be supplied to the mixture. The mixture was then cooled and the salts were filtered off and destroyed in saturated iron sulphate solution and the filtrate was distilled on a column. 507 g (74% of theory) of a colorless oil with a boiling point of 126° C./20 mm Hg were thus obtained.

EXAMPLE 2

4-Fluoro-3-bromo-phenylglyoxylic acid (a)

A mixture of 228 g of 4-fluoro-3-bromo-benzoyl cyanide and 1,625 ml of concentrated hydrochloric acid were stirred at room temperature for 20 hours. The mixture was then heated slowly to 70° to 80° C. and stirred at this temperature for 8 hours. For crystallization the reaction mixture was stirred for a further 17 hours at room temperature, and the crystals were then filtered off, rinsed with 1,000 ml of water and dried in vacuo at 35° to 40° C. for 24 hours. 246 g (99.6% of theory) of 4-fluoro-3-bromo-phenylglyoxylic acid were thus obtained as a colorless powder with a melting point of 68° to 73° C.

(b)

A weak stream of hydrogen chloride was passed into a solution of 45.6 g (0.2 mole) of 4-fluoro-3-bromo-benzoyl cyanide in 200 ml of concentrated hydrochloric acid for 5 hours. During this procedure, the temperature rose to +30° C. The mixture was then stirred at 80° C. for 6 hours and subsequently cooled and the crystals which had precipitated were filtered off. 43 g (87% of theory) of 4-fluoro-3-bromo-phenyl-glyoxylic acid were obtained in the form of colorless crystals.

EXAMPLE 3a

4-Fluoro-3-bromo-benzaldehyde anil 102.3 g (1.1 moles) of freshly distilled aniline were added dropwise to a mixture of 1,300 ml of toluene or chlorobenzene and 247 g of 4-fluoro-3-bromophenyl-glyoxylic acid at 70° to 80° C. The reaction mixture was then heated to the reflux temperature, and was stirred under reflux for a further 4 hours in order to bring the decarboxylation to completion. Thereafter, the solvent was stripped off in vacuo. 270 g (97% of theory) of the anil remained in the form of a colorless powder with a melting point of 45° to 47° C.

EXAMPLE 3b

A solution of 101.5 g (0.5 mole) of 4-fluoro-3-bromo-benzaldehyde and 46.5 g (0.5 mole) of aniline in 250 ml of toluene was boiled for 1 hour, using a water separator. The solvent was then distilled off in vacuo. 129 g (93% of theory) of 4-fluoro-3-bromo-benzaldehyde anil remained in the form of colorless crystals with a melting point of 47° to 49° C.

The following compounds of the formula:

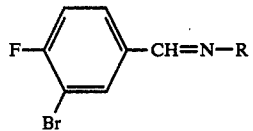

as indicated in following Examples 3c to 3f, could be prepared in a manner analogous to that described in the appropriate one of the two Examples 3a or 3b:

| Example | R | Melting point (°C.) |
|---|---|---|
| 3c | ⌬- | partially crystalline |
| 3d | ⌬- | partially crystalline |
| 3e | H₃C-⌬- | 62 |
| 3f | Cl-⌬- | 82 |

EXAMPLE 4

4-Fluoro-3-bromobenzaldehyde dimethyl acetal ("one-pot" process starting with the glyoxylic acid)

102.3 g (1.1 moles) of freshly distilled aniline were added dropwise to a mixture of 1,300 ml of toluene or chlorobenzene and 247 g of 4-fluoro-3-bromo-phenyl-glyoxylic acid at 70° to 80° C. The reaction mixture was then heated to the reflux temperature and was stirred under reflux for a further 4 hours in order to bring the decarboxylation to completion. Thereafter, the solvent was stripped off under a waterpump vacuum and the residue was subjected to incipient distillation under 0.5 to 0.01 mm Hg. The residue was dissolved in 1,000 ml of anhydrous methanol, and 54 g of sulphuric acid monohydrate were added dropwise at 20° to 25° C. The mixture was stirred at room temperature for 4 hours, the methanol was evaporated off under a waterpump vacuum, the residue was taken up in toluene, the mixture was filtered and the filtrate was washed once with dilute potassium carbonate solution. After drying the organic phase with sodium sulphate, it was concentrated under a waterpump vacuum and distilled under 0.1 mm Hg. After first runnings at 35° to 40° C., the acetal was distilled off at 65° to 70° C. 209 g (84% of theory) of a colorless oil were obtained in this manner.

EXAMPLE 5

4-Fluoro-3-bromobenzaldehyde dimethyl acetal from the anil 5.4 g (0.55 mole) of anhydrous sulphuric acid were added dropwise to a solution of 27.8 g (0.1 mole) of 4-fluoro-3-bromobenzaldehyde anil in 100 ml of absolute methanol at 20° to 25° C., and the mixture was subsequently stirred at room temperature for 4 hours. The solvent was then stripped off in vacuo, 200 ml of toluene were added to the residue and the insoluble material was filtered off. The filtrate was washed with 50 ml of 5% strength potassium carbonate solution, dried over sodium sulphate and evaporated. The residue was distilled in vacuo. 22.9 g (92% of theory) of the acetal were thus obtained in the form of a colorless oil with a boiling point of 79° C./0.5 mm Hg.

The following compounds could be prepared in an analogous manner:

| | Boiling point |
|---|---|
| F-⌬-CH(OC₂H₅)₂ (Br) | 70–72° C./0.2 mm Hg |
| F-⌬-CH(OC₃H₇iso)₂ (Br) | 67–70° C./0.1 mm Hg. |

It will be understood that the specification and examples are illustrative but not limitative of the present invention and that other embodiments within the spirit and scope of the invention will suggest themselves to those skilled in the art.

We claim:

1. A process for the preparation of a 3-bromo-4-fluoro-benzaldehyde acetal of the formula:

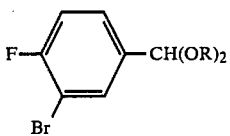

in which R each independently is a $C_1$ to $C_4$ alkyl group or the radicals R together are a $C_2$ to $C_5$ alkanediyl radical, comprising reacting a 3-bromo-4-fluoro-benzaldimine of the formula:

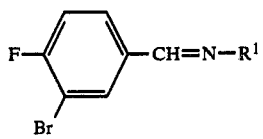

in which $R^1$ is an alkyl, cycloalkyl or aryl radical, with an alcohol or alkanediol of the formula:

(HO)$_n$—R in which n is 1 or 2, in the presence of sulphuric acid at a temperature between about 0° and 100° C.

2. A process according to claim 1, wherein the 3-bromo-4-fluorobenzaldimine is produced by reacting 3-bromo-4-fluoro-phenylglyoxylic acid of the formula:

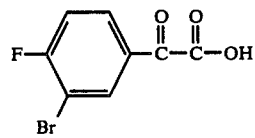

with an amine of the formula:

$H_2N-R^1$ at a temperature between about 0° and 200° C.

3. A process according to claim 1, wherein the reaction is carried out at a temperature between about 10° and 50° C.

4. A process according to claim 1, wherein the alcohol is methanol, ethanol or ethane-1,2-diol.

5. A process according to claim 2, wherein the reaction between the 3-bromo-4-fluoro-phenylglyoxylic acid and the amine is carried out in the presence of a diluent.

6. A process according to claim 2, wherein the reaction between the 3-bromo-4-fluoro-phenylglyoxylic acid and the amine is carried out at a temperature between about 50° and 150° C.

7. A process according to claim 1, wherein $R^1$ is a $C_5$ or $C_6$ cycloalkyl radical or a phenyl radical which is optionally substituted by methyl, ethyl, chlorine and/or nitro.

8. A 3-bromo-4-fluoro-benzaldimine of the formula:

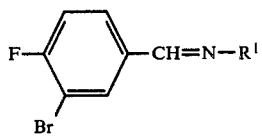

in which $R^1$ is an alkyl, cycloalkyl or aryl radical.

9. A process for the preparation of a compound according to claim 8, comprising reacting 3-bromo-4-fluoro-benzaldehyde of the formula:

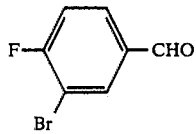

with an amine of the formula:

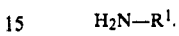

$H_2N-R^1$.

10. A process for the preparation of a compound according to claim 8, comprising reacting 3-bromo-4-fluoro-phenylglyoxylic acid with an amine of the formula:

$H_2N-R^1$.

11. A process according to claim 8 or 9, wherein the reaction is carried out in the presence of a diluent at a temperature between about 50° and 150° C.

12. 3-Bromo-4-fluoro-phenylglyoxylic acid of the formula:

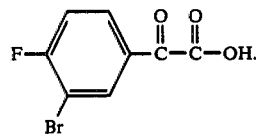

13. A process for the preparation of 3-bromo-4-fluoro-phenylglyoxylic acid according to claim 12, comprising reacting 3-bromo-4-fluoro-benzoyl cyanide of the formula:

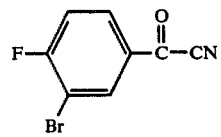

with hydrochloric acid or sulphuric acid.

14. A process according to claim 13, wherein the reaction is carried out using hydrochloric acid.

15. A process according to claim 13, wherein the reaction is carried out at a temperature between about 20° and 80° C.

16. 3-Bromo-4-fluoro-benzoyl cyanide of the formula:

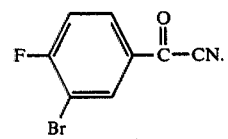

17. A process for the preparation of 3-bromo-4-fluoro-benzoyl cyanide according to claim 16, comprising reacting 3-bromo-4-fluoro-benzoyl halide of the formula:

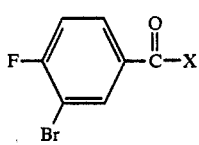

in which X is a fluorine, chlorine or bromine atom with sodium cyanide or potassium cyanide.

18. A process according to claim 17, wherein the reaction is carried out at a temperature between about 20° and 120° C.

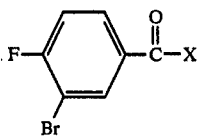

in which X is a fluorine, chlorine or bromine atom with sodium cyanide or potassium cyanide.

18. A process according to claim 17, wherein the reaction is carried out at a temperature between about 20° and 120° C.